United States Patent [19]

Taylor et al.

[11] Patent Number: 4,522,205
[45] Date of Patent: Jun. 11, 1985

[54] THERAPEUTIC DEVICE AND METHOD OF INDUCING THROMBOSIS IN A BLOOD VESSEL

[75] Inventors: Thomas V. Taylor, Altrincham, England; James M. Neilson, Edinburgh, Scotland

[73] Assignee: The University Court of The University of Edinburgh, Edinburgh, Scotland

[21] Appl. No.: 375,287
[22] PCT Filed: Sep. 3, 1981
[86] PCT No.: PCT/GB81/00176
§ 371 Date: May 3, 1982
§ 102(e) Date: May 3, 1982
[87] PCT Pub. No.: WO82/00768
PCT Pub. Date: Mar. 18, 1982

[30] Foreign Application Priority Data

Sep. 3, 1980 [GB] United Kingdom ............... 8028356

[51] Int. Cl.³ ............................................. A61N 1/04
[52] U.S. Cl. ............................. 128/303.17; 128/785; 128/641
[58] Field of Search ................. 128/303.17, 639, 642, 128/786, 303.15, 303.14, 303.13, 785, 325

[56] References Cited

U.S. PATENT DOCUMENTS

| | | | |
|---|---|---|---|
| 2,068,721 | 1/1937 | Wappler et al. | 128/303.15 |
| 3,326,207 | 6/1967 | Egan | 128/642 |
| 3,411,506 | 11/1968 | Velasco | 128/325 |
| 3,802,698 | 4/1974 | Burian et al. | 128/644 X |
| 3,837,347 | 9/1974 | Tower | 128/786 X |
| 3,850,176 | 11/1974 | Gottschalk | 128/325 |
| 3,888,240 | 6/1975 | Reinhold, Jr. et al. | 128/644 |
| 3,920,021 | 11/1975 | Hiltebrandt | 128/303.17 |
| 4,033,357 | 7/1977 | Helland et al. | 128/785 |
| 4,092,986 | 6/1978 | Schneiderman | 128/303.17 X |
| 4,117,846 | 10/1978 | Williams | 128/303.13 |
| 4,124,028 | 11/1978 | Gallo | 128/407 |
| 4,198,963 | 4/1980 | Barkalow et al. | 128/642 X |
| 4,304,239 | 12/1981 | Perlin | 128/786 X |

FOREIGN PATENT DOCUMENTS

| | | |
|---|---|---|
| 0012122 | 11/1979 | European Pat. Off. . |
| 1589021 | 9/1969 | Fed. Rep. of Germany . |
| 1514356 | 12/1969 | Fed. Rep. of Germany . |
| 1466248 | 12/1966 | France . |

OTHER PUBLICATIONS

Schaudinischky, L. et al. "Technical Note: The Shape Conforming Electrode", *Med. and Biol. Engng.* vol. 7, No. 3, May 1969, pp. 341-343.

*Primary Examiner*—Edward M. Coven
*Attorney, Agent, or Firm*—Dennison, Meserole, Pollack & Scheiner

[57] ABSTRACT

Apparatus for inducing thrombosis in a blood vessel subjacent a surface 14 of a living human or animal body comprises a therapeutic electrode 15, 21, 22, 23, 24, in the form of an inflatable balloon which is flexible enough to conform to the surface, and which maintains the electrode in contact with the surface and restricts the flow of blood through the blood vessel during induction of thrombosis therein. Direct current is flowed through the electrode as anode and a counter cathode to coagulate the blood in the blood vessel adjacent the anode. The apparatus is useful to treat active oesophageal variceal bleeding, in which application the electrode 15 may have the general form of a Sengstaken-Blakemore oesophageal tamponade tube.

22 Claims, 4 Drawing Figures

THERAPEUTIC DEVICE AND METHOD OF INDUCING THROMBOSIS IN A BLOOD VESSEL

TECHNICAL FIELD

This invention relates to a therapeutic device and a method for its use and, more particularly, to apparatus for inducing thrombosis in a blood vessel to control haemorrhage or potential bleeding. Haemorrhage or potential bleeding is a problem in many surgical situations, for example, gastro-intestinal tract bleeding, urinary tract bleeding and per- and post-operative bleeding. Specific examples are haemorrhage from varicose veins (varices) of the oesophagus, from the prostatic bed after prostatectomy, from haemorrhoids, from the liver after cholectystectomy (removal of the gall bladder) or liver resection, from operative manipulation and trauma, from aneurysms and from varicose veins other than of the oesophagus. In some cases, the occurrence of acute ailments, for example, varices of the oesophagus, is rapidly increasing, accounting for tens of thousands of fatalities annually.

BACKGROUND ART

Acute bleeding of oesophageal varices is commonly treated by use of a tamponade tube, such as the Sengstaken-Blakemore tube which was first introduced in 1950, which tube restricts the flow of blood through the vessel, thereby assisting blood coagulation by natural mechanisms. One study has indicated that it will provide initial control of bleeding in over 80% of patients. However, in over 60% of these patients rebleeding will occur when the tube is withdrawn. In the patients who rebleed, there is a 60% rate of mortality.

A number of methods of further treatment are available once bleeding has been arrested. Injection of the varices with a sclerosing agent is feasible only with variceal observation e.g. by an endoscope unobscured by bleeding. Mortalities of around 50% have been found with emergency portasystemic shunting or with gastric or oesophageal surgery. There is a high incidence of rebleeding associated with the use of vasopressin. Thus, none of the methods so far proposed is associated with a high rate of success.

The application of electrical current to induce thrombosis was employed by Lutz in 1951; see Circulation 1951; 3:339–351. Sawyer has demonstrated that passage of current across a normal blood vessel precipitates a thrombus only at the anode; See Amer.J.Physiol. 1960; 198:1006–1010.

DISCLOSURE OF INVENTION

The present invention has as one object to provide an apparatus method which makes possible long-term control of haemorrhage in blood vessels by a non-surgical method, and which is less hazardous to the patient than the methods previously proposed.

According to the present invention there is provided apparatus for inducing thrombosis in a blood vessel subjacent a surface of a living human or animal body, characterised in that it comprises a therapeutic electrode which is flexible enough to conform to said surface, means for maintaining the electrode in contact with the surface and for restricting the flow of blood through the blood vessel during induction of thrombosis therein, the apparatus being provided with leads for electrical connection of the electrode to a source of direct electrical current and so constructed as to support passage of said electrical current through the blood vessel between the therapeutic electrode as anode and a counter cathode for a period of time and at a current density at the surface of the anode sufficient to induce thrombosis in the blood vessel, the anode being non-toxic and resistant to anodic electrochemical dissolution during said period of time.

The means for maintaining the electrode in contact and the means for restricting flow will normally be the same but need not be. The apparatus is totally unlike a diathermy device and does not rely on electrically-generated heat for its effectiveness.

It is an important feature of the invention that it permits treatment of blood vessels during acute bleeding thereof, in distinction from those prior art treatments which can be carried out only after bleeding has been arrested temporarily. With the apparatus of the invention a potential for long-term control is present in the same treatment that provides initial arrest of bleeding. Furthermore, the apparatus may be very useful in preventative methods of treatment where there is a potential for acute bleeding.

Tests have indicated that the likelihood of thrombus formed by use of the apparatus of the invention subsequently moving along the blood circulation system of the patient is acceptably small.

The thrombus may result in complete blockage of an oesophageal varix or other blood vessel and its consequent removal from the blood circulation system.

Such an effect has been observed with the use of sclerosing agents and, for treatment of oesophageal varices, is not undesirable. In other situations where use of the apparatus is indicated it is also unlikely to be found undesirable.

Test results of the apparatus to date are limited but give every indication that the apparatus can provide treatment of oesophageal varices which is highly effective. Eight poor risk patients with active oesophageal variceal bleeding were treated. The apparatus used comprised an inflatable oesophageal balloon on the external surface of which were four, longitudinally-extending electrodes which functioned as anodes in use of the apparatus. Post mortem examination of four of these patients confirmed earlier animal experiments and revealed no evidence of dilated submucosal varices. Histological sectioning of the oesophagus showed haemosiderin-laden microphages with evidence of new vessel formation consistent with a previous thrombosis. No cardiac arrythmias were recorded during use of the apparatus.

Gastric varices could be treated by an apparatus according to the invention incorporating a dilatable gastric balloon and these may be treated simultaneously with oesophageal varices. Apparatus in the form of a urethral catheter could enable treatment of bleeding blood vessels in the urethra, and bleeding of a prostatectomy wound site could be arrested by use of an apparatus according to the invention in the form of a bladder catheter. Other treatments of blood vessels beneath the surface of bodily cavities will occur to those skilled in the art, while the apparatus may also find use in the treatment of bodily extremities and organs where the therapeutic electrode has a cavity or aperture to receive the extremity or organ.

BRIEF DESCRIPTION OF DRAWINGS

For a better understanding of the invention, and to show more clearly how the same may be carried into effect, reference will now be made, by way of example, to the accompanying drawings, in which.

BEST MODE OF CARRYING OUT THE INVENTION

Figure 1:
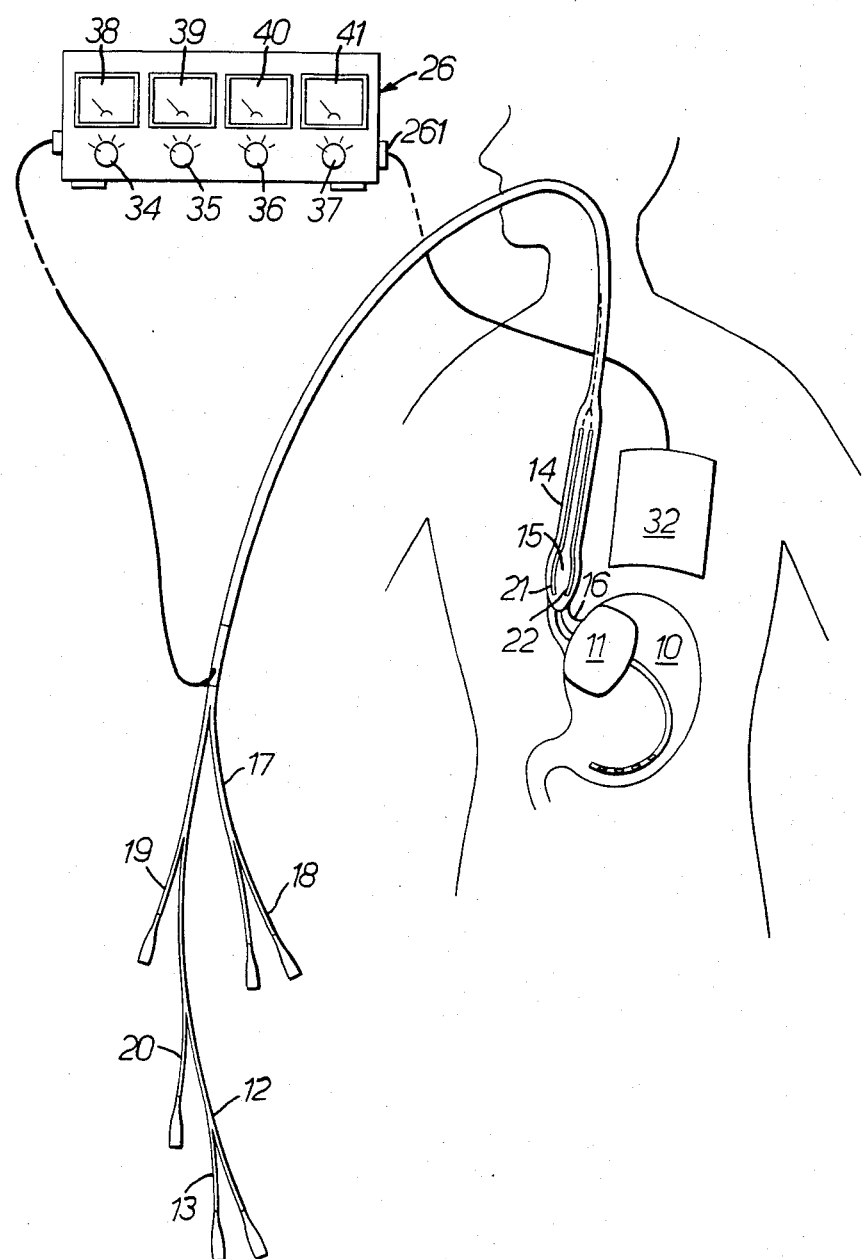
FIG. 1 shows diagrammatically an apparatus according to the invention, which comprises an oesophageal tamponade tube, inserted within the oesophagus and stomach of a human patient.

The construction of the tamponade tube shown in FIG. 1 has as its basis the construction of a 4-lumen Sengstaken-Blakemore tamponade tube, and as such will be familiar to those skilled in the art.

At the end of the tube which enters the stomach 10 is a distensible latex gastric balloon 11 which is inflated in use by admission of gas to a first lumen 12. This first lumen has a gas pressure monitoring outlet 13.

That part of the tube which is located within the oesophagus 14 has the form of an inflatable, latex oesophageal balloon 15 through which the first lumen 12 passes. The balloon 15 extends to the sphincter 16 between the stomach 10 and the oesophagus 14. It is inflated by admission of gas to a second lumen 17 which has a gas monitoring outlet 18. Third 19 and fourth 20 lumens provide means for aspirating the stomach 10 and oesophagus 14.

Figure 2:
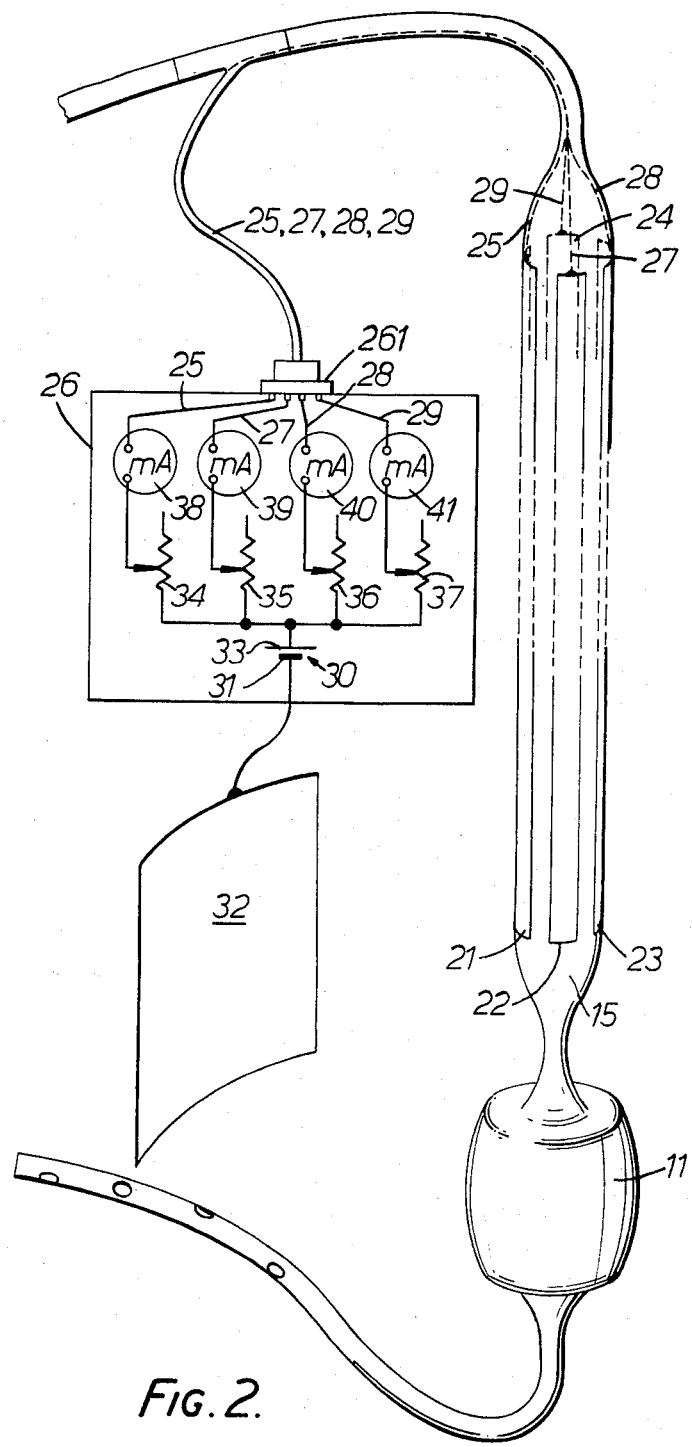
FIG. 2 is a schematic diagram of an electrical circuit which is completed during use of the apparatus.

On the external surface of the oesophageal balloon 15 are four electrodes 21, 22, 23 and 24 (shown more clearly in FIG. 2). Each electrode is a thin strip of silver metal, plated with a layer of gold of thickness 3 microns, and bonded onto the balloon surface by the use of an elastic adhesive composition. The four strip electrodes are equally spaced from one another around the circumference of the balloon 15 and extend longitudinally of the balloon such that a distal end of each electrode is as close as possible to the sphincter 16. Four electrode elements are shown in this embodiment; the number of elements utilized according to the invention will normally be at least two.

Figure 3:
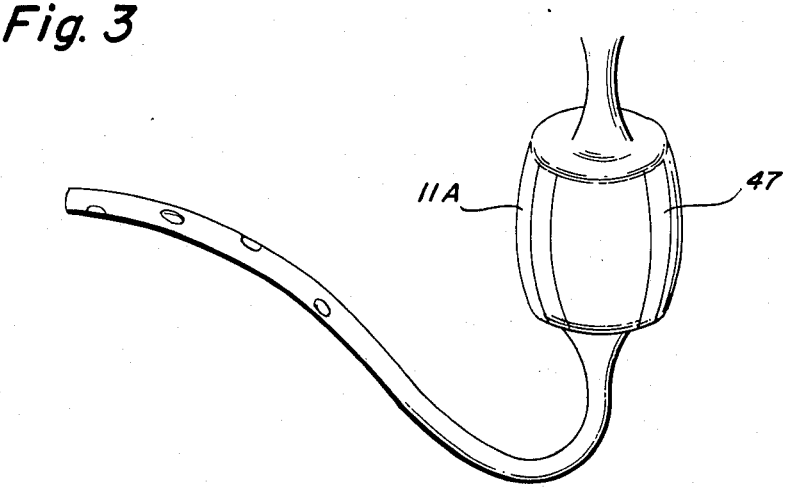
FIG. 3 shows a variation of the gastric balloon shown in FIG. 1.

In alternative embodiments the electrodes 21 to 24 may comprise electroconductive areas of the balloon 15 itself, and bleeding of gastric varices might be treatable by the provision of electrodes in analogous fashion on the gastric balloon, as shown in FIG. 3, in which electrodes 47 are provided on gastric balloon 11A. Electrodes on the gastric balloon may be provided, either in addition to oesophageal electrodes or instead of such electrodes. The electrodes may also be composed, wholly or in part, of an electroconductive plastics material. This plastics material may typically comprise an electrically insulating matrix filled with a multitude of mutually contacting metallic particles.

An insulated lead 25 (FIG. 2) extends from the electrode 21 along the fourth lumen 20 to a jack plug and socket 261 of electrical equipment 26 associated with the apparatus. Like leads 27, 28 and 29 extend from electrodes 22, 23 and 24 respectively through the lumen 20 to the same jack plug 261.

In an earlier embodiment, gold plated metal strip electrodes of the same general shape and form as illustrated herein, were secured to the external surface of the balloon 15 by bands of NYLON (trade mark) tape and the ends of the electrode strips buried in an elastic adhesive. The leads 25, 27, 28 and 29 were taped to the external surface of the four lumen assembly of the tamponade tube. Considerable attention is paid, in all embodiments, to the need to minimise additional difficulties of intubation and extubation caused by the presence of the electrodes on the oesophageal balloon.

Turning now to FIG. 2, the electrical equipment 26 comprises a source 30 of electro-motive force and direct electrical current, to the negative pole 31 of which is connected, in use of the apparatus, a flat plate counter cathode 32 which is fitted to the patient in the scapular region. To the positive pole 33 is connected an array of four adjustable resistances 34, 35, 36 and 37 in parallel with one another. Resistance 34 is connected to the electrode 21 via a milliammeter 38, the jack plug 261 and the lead 25. In like manner, resistance 35 is connected to the electrode 22 through a milliammeter 39, resistance 36 to electrode 23 through a milliammeter 40 and resistance 37 to electrode 24 through a milliammeter 41. Although not shown, voltmeters may be provided to monitor the instantaneous voltage across each of the electrodes 21 to 24.

The electrical equipment 26 is shown only schematically. In practice it is likely to be a semiconductor device which constitutes a generator of a constant selected current through each of the electrodes 21 to 24.

Figure 4:
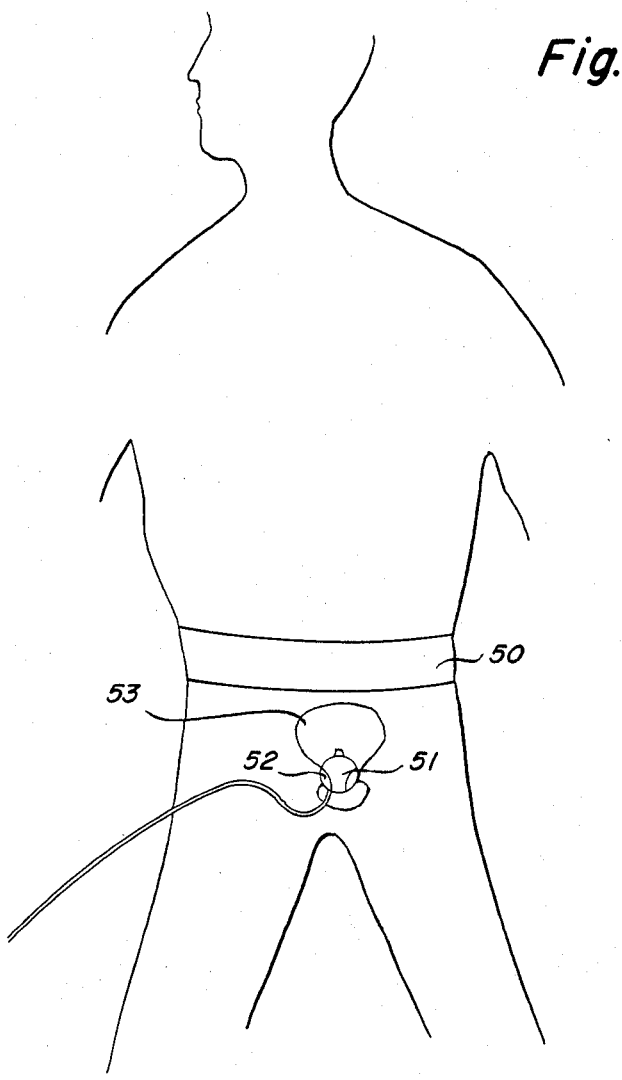
FIG. 4 shows diagrammatically an apparatus according to the invention comprising a bladder catheter and counter-electrode in the form of a belt.

In the oesophagus, the electrodes 21 to 24 are likely to be all at different distances from the cathode 32, so that a different voltage is required across each in order to establish the same current density at their respective surfaces. With the cathode 32 in the scapular region an even density of current can be achieved around the oesophagus and electrical interference with the heart of the patient is minimised.

Where apparatus according to the invention is to be used to treat bleeding after prostatectomy as shown in FIG. 4, the cathode could be in the form of a belt 50 around the waist of the patient, in order to provide uniform or near uniform current density at the therapeutic electrode. A bladder catheter 51, with electrodes 52 can be used in conjunction with the belt as the treatment means for bladder 53.

In use, the gastric and oesophageal balloons are deflated and the tamponade tube inserted in the usual way. As the electrodes are thin, flexible and narrow, and extend longitudinally of the tube, they do not unduly interfere with this operation. Once the tube is inserted the positions of the electrodes correspond to those of the varices, which themselves run longitudinally of the oesophagus.

The gastric balloon 11 is inflated, by passage into it of a predetermined volume of gas, to secure the oesophageal balloon in position. Then the oesophageal balloon 15 is inflated to a pressure of typically, 30 mmHg, which inflation applies physical pressure to the varices and brings about hemostasis, and is practised conventionally. Now, however, the electrical equipment 26 is actuated. With a total current of around 80 mA and a voltage in the range of 1 to 10 volts, and typically around 7 volts, a current density at the surface of the therapeutic anodes in a range of from 1 to 10 mA/cm$^2$ is established and maintained for a long period, typically within a range of from 1 hr to 12 hrs. All the while, the products removed by the aspirating lumens 19 and 20 are examined for evidence of arrest of bleeding. Following treatment of the bleeding varix or varices by physical pressure from the oesophageal balloon to restrict flow of blood therethrough and passage of direct electrical current from the adjacent anode to thrombose the or each varix, the current is switched off, the oesophageal balloon deflated and the patient observed for a further period of some hours for evidence that bleeding has not re-commenced. If all indications are satisfactory, the gastric balloon is deflated and the tamponade tube is gently withdrawn.

We claim:

1. Apparatus for inducing thrombosis in a blood vessel in surface tissue at a particular site on a living human or animal body, comprising a therapeutic electrode in the form of an inflatable balloon having an electrically conductive surface area, wherein inflation of the balloon maintains said surface area, by fluid pressure, in contact with the tissue, a counter-electrode separate from the balloon, and a source of time-steady direct electrical current for connection to the therapeutic electrode as anode and the counter-electrode, as cathode wherein said therapeutic electrode is adapted to be inflated to a gauge pressure of at least 30 mm Hg, and comprises at least two spaced, electrically conductive electrode elements, each including an individual connection to said source of direct current, and wherein the apparatus includes means to monitor and adjust the current flowing through each electrode element such that the current density at the surface of any electrode element can be made equal to the current density at the surface of any other electrode element.

2. Apparatus as claimed in claim 1 wherein said electrode elements are metal elements bonded to the external surface of the inflatable balloon.

3. Apparatus as claimed in claim 1 wherein the electrode elements are electro-conductive areas in the wall of the inflatable balloon.

4. Apparatus as claimed in claim 1 wherein the particular site is an oesophagus, the therapeutic electrode is so constructed as to be capable of being inserted in, and subsequently removed from, the oesophagus, and the counter electrode is a scapular electrode.

5. Apparatus as claimed in claim 4 wherein the therapeutic electrode includes an inflatable gastric balloon to secure the electrode in position in the oesphagus.

6. Apparatus as claimed in claim 4 wherein the oesophageal balloon has the form of an electrically-insulated inflatable oesophageal tamponade tube on which said electrode elements are provided in the form of electrically-conductive electrode strips which run lengthwise on the tube and which, in use of the electrode, extend to the region of the oesphago-gastric junction.

7. Apparatus as claimed in claim 1 wherein the particular site is a prostatectomy cavity, the therapeutic electrode is so constructed as to be capable of being inserted in, and subsequently removed from, the cavity, and the counter-electrode resembles a belt to encircle the torso of the body undergoing treatment.

8. Apparatus as claimed in claim 7 wherein the therapeutic electrode comprises a bladder catheter.

9. Apparatus as claimed in claim 1 wherein the particular site is that of gastric varices, and the therapeutic electrode comprises an inflatable gastric balloon having a shape which allows for insertion in, and removal from, the stomach of the body undergoing treatment.

10. Apparatus as claimed in claim 9 wherein the electrode elements are provided on the gastric balloon as electrode strips.

11. Apparatus as claimed in claim 1 wherein the therapeutic electrode comprises a multitude of mutually-contacting electrically-conductive particles embedded in at least two spaced areas of an electrically-insulating matrix.

12. Apparatus as claimed in claim 1 wherein the source of direct electrical current comprises a current generator for providing to each of the electrode elements a flow of current which is controllable within a range of from 1 to 10 volts and 1 to 10 mA/sq cm of the active surface area of the electrode element.

13. Apparatus as claimed in claim 12 wherein the current generator comprises means to automatically maintain constant the current flowing through each electrode element at a predetermined level.

14. Apparatus as claimed in claim 1 wherein said electrode elements are connected to said source as anodes, and said counter-electrode is connected as a cathode.

15. A method of inducing thrombosis in a blood vessel in surface tissue of a living human or animal body comprising the steps of:
  (i) positioning on said surface a therapeutic electrode which is a balloon inflatable to a gauge pressure of at least 30 mm Hg and comprising at an area of the surface of the balloon, at least two spaced, electrically conductive electrode elements each with an individual connection to a source of direct current;
  (ii) inflating the balloon to maintain said area of the surface in contact with the surface tissue and restrict the flow of blood through the blood vessel;
  (iii) applying to the body a counter-electrode;
  (iv) providing through the electrode elements, the blood vessel and the counter-electrode a time-steady direct current, with the electrode elements serving as anodes; and
  (v) monitoring and adjusting the current flowing through each electrode element so that the current density at the surface of any electrode element is equal to the current density of any other said electrode element.

16. The method according to claim 15 wherein the balloon is inflated to a pressure of at least 30 mm Hg.

17. The method according to claim 15 wherein the voltage applied between the electrode elements as anodes and the counter-electrode as cathode is in a range of from 1 to 10 volts.

18. The method according to claim 17 wherein the monitoring and adjusting step is to secure a current density at the surface of each electrode element which is in a range of from 1 to 10 mA/cm$^2$.

19. The method according to claim 15 wherein the surface is an oesophagus and the blood vessel is an oesophageal varix, the balloon is positioned such that the electrode elements extend to the oesphago-gastric junction and the counter-electrode is applied to the scapular region of the body.

20. The method according to claim 15 comprising the step of securing the balloon in position by inflating within the stomach adjacent the oesophago-gastric junction, a gastric balloon secured to the therapeutic electrode, prior to inflation of the balloon carrying the electrode elements.

21. The method according to claim 15 wherein the electrode is positioned in a prostatectomy cavity and the counter-electrode is positioned on the body as a belt around the torso of the body.

22. The method according to claim 15 wherein the electrode is positioned in the stomach of the body for treatment of a gastric varix.

* * * * *